United States Patent
Tavares

(10) Patent No.: US 6,998,371 B2
(45) Date of Patent: Feb. 14, 2006

(54) NAIL POLISH REMOVER COMPRISING FATTY ACID ESTER AND ALKYL LACTATE

(75) Inventor: Bruce Anthony Tavares, Hartland, WI (US)

(73) Assignee: React-NTI, LLC, Lino Lakes, MN (US)

( * ) Notice: Subject to any disclaimer, the term of this patent is extended or adjusted under 35 U.S.C. 154(b) by 22 days.

(21) Appl. No.: 10/753,015

(22) Filed: Jan. 7, 2004

(65) Prior Publication Data

US 2004/0142830 A1   Jul. 22, 2004

Related U.S. Application Data

(60) Provisional application No. 60/438,823, filed on Jan. 9, 2003.

(51) Int. Cl.
*C11D 3/20*   (2006.01)
*C11D 3/44*   (2006.01)

(52) U.S. Cl. .................. 510/118; 510/201; 510/208; 510/211; 510/432; 510/437; 134/38

(58) Field of Classification Search ............... 510/118, 510/201, 208, 211, 432, 437; 134/38
See application file for complete search history.

(56) References Cited

U.S. PATENT DOCUMENTS

| | | | | |
|---|---|---|---|---|
| 5,346,652 A | * | 9/1994 | Dotolo et al. | 510/118 |
| 5,372,742 A | * | 12/1994 | Bayless | 510/118 |
| 5,866,104 A | | 2/1999 | Cataneo et al. | |
| 6,096,699 A | * | 8/2000 | Bergemann et al. | 510/201 |
| 6,156,711 A | * | 12/2000 | Perlman | 510/118 |
| 6,254,878 B1 | | 7/2001 | Bednarek et al. | |
| 6,284,720 B1 | * | 9/2001 | Opre | 510/170 |
| 6,689,727 B1 | * | 2/2004 | Olsson | 510/118 |

* cited by examiner

*Primary Examiner*—Charles Boyer
(74) *Attorney, Agent, or Firm*—Alfred D. Lobo

(57) ABSTRACT

A nail polish remover is formulated from a combination of solvents derived from naturally occurring materials, which combination consists essentially of a (i) a major proportion by weight ("by wt") of esters of fatty acids having from 16 to 18 carbon atoms wherein the content of linoleic acid ester in the source vegetable oil is less than 60%, and (ii) a minor proportion by weight of a lower ($C_1$–$C_5$) alkyl lactate. The nail polish remover is highly effective yet has good skin conditioning properties, is non-toxic and non-flammable. A visible residue several micrometers thick provides a desirable gloss on the cleaned nails unless it is washed off.

7 Claims, No Drawings

NAIL POLISH REMOVER COMPRISING FATTY ACID ESTER AND ALKYL LACTATE

CROSS-REFERENCE TO RELATED APPLICATION

This application claims the benefit of U.S. Provisional Application Ser. No. 60/438,823 filed on 09 Jan. 2003.

FIELD OF THE INVENTION

This invention relates to a nail polish remover which is derived from naturally occurring organic materials; the nail polish remover is essentially non-flammable, non-toxic, has a soothing effect on skin and cuticle when applied to finger and toe nails, and is biodegradable.

BACKGROUND OF THE INVENTION

Nail polish, irrespective of its composition, is required to be removed from the surface of finger nails and toe nails without damaging the nail or the health of a person who uses it. Equally important, but not generally stated, is that using the polish should not dry out either the nail or the skin and cuticle surrounding the nail, or the skin of the finger or toe.

At the present time, nail polish typically consists essentially of a polymeric binder resin and pigment referred to as lacquers or enamels; primarily used are nitrates of cellulose, either as a pigment dispersant or as a film-forming binder; also used are acrylic polymers, mainly copolymers of (meth)acrylic acid, (meth)acrylic acid esters and styrene as disclosed in U.S. Pat. No. 6,254,878. The term "(meth)acrylic acid" is used to connote both, unsubstituted acrylic acid and its methyl-substituted derivative.

To remove lacquers and enamels, it is essential that a commercial nail polish remover have good polish-dissolving and removal characteristics, good skin conditioning properties, low volatility, low flammability, and low odor; in addition, the nail polish remover should be easy to clean off the finger nails with soap and water.

Until recently, compositions for removing nail polish have relied upon acetone, ethyl acetate and mixtures of these in which one or the other predominates. Acetone is a flammable and toxic liquid which rapidly evaporates upon exposure to room temperature conditions and emits a characteristic odor not easy to mask. Moreover, acetone is so powerful a solvent as to penetrate skin easily; upon evaporating, acetone dries out the keratin of the nail. Thereafter, acetone leaves a visible residue on the nail which residue is difficult to remove from the cleaned nail. Other solvents typically used in nail polish removers include ethyl acetate, and combinations including ethylene and/or propylene carbonate or diethers and diesters, each of which has several undesirable effects similar to those of acetone. Numerous attempts have been made to develop polish removers that avoid the problems of known removers, but there is still a need for a nail polish remover which is less damaging to skin and cuticles than acetone, and which is formulated mainly from environmentally friendly, easy to use higher fatty acid esters derived from naturally occurring vegetable oils, referred to as "source vegetable oils", in combination with a lower alkyl ester of lactic acid. By "lower alkyl" is meant that the alkyl group has from 1 to 5 carbon atoms; by "higher fatty acid" is meant that the fatty acid has more than 12 carbon atoms.

SUMMARY OF THE INVENTION

A nail polish remover which has polish removal characteristics comparable to a mixture of acetone and ethyl acetate, has desirable skin conditioning properties, sufficiently low volatility and flammability to meet the latest requirements of every State in the United States of America and most foreign countries, and low odor when not deliberately scented, consists essentially of (i) a major proportion by weight ("by wt") of esters of fatty acids having from 16 to 18 carbon atoms wherein the content of linoleic acid ester in the source vegetable oil is less than 60%, and (ii) a minor proportion by weight of a lower ($C_1$–$C_5$) alkyl lactate, preferably ethyl lactate, meets all environmental requirements and provides excellent protection against drying skin. Fatty acid esters derived from source vegetable oils which contain at least 60% by weight of linoleic acid ester are linseed oil and soybean oil. Most preferably, a major proportion by wt of the fatty acid esters are unsaturated, that is, have at least two double bonds, and though the $C_{16}$–$C_{18}$ fatty acid esters may contain contaminant higher fatty acid esters outside the $C_{16}$–$C_{18}$ range, that is, fatty acids have from 12 to 14 carbon atoms as well as from 20–24 carbon atoms, due to the commercial separation process used to provide the desired fatty acid ester fraction, these contaminant higher fatty acid esters are desirably present in an amount less than 10% by wt of all the higher fatty acid esters.

It is critical for good skin conditioning that a major proportion by weight of the higher fatty acid esters be of higher fatty acids which are diolefinic and triolefinic fatty acids, and that the combined weight of these esters exceed the weight of the other higher fatty acids.

The nail polish remover may include from about 5 to 10% by wt of an emollient and/or thickening agent, if additional skin conditioning and/or thickening is desired. A preferred emollient is glycerol; a preferred thickening agent is preferably a naturally occurring wax that provides a gel which is not fluid at room temperature (23° C.) and atmospheric pressure.

The nail polish remover may also include from 0 to less than 1% by wt of a cosmetic enhancer chosen from a coloring additive, dye or lake and a fragrance.

DETAILED DESCRIPTION OF PREFERRED EMBODIMENTS

The nail polish remover is preferably readily formulated by mixing from more than 50% to about 75% by wt of a mixture of commercially available lower alkyl esters of $C_{16}$–$C_{18}$ fatty acid esters derived from cottonseed oil, olive oil, arachis (peanut) oil, maize oil and the like. Most preferred are esters obtained by the esterification (preferably methylation) of palmitic ($C_{16}H_{32}O_2$ or $CH_3(CH_2)_{14}COOH$, oleic $C_{18}H_{34}O_2$ or $CH_3(CH_2)_{14}(CH)_2COOH$ and linoleic $C_{18}H_{32}O_2$, or $(CH)_3(CH_2)_{12}(CH_4)COOH$ acids derived as a mixture from cottonseed oil, such as the commercially available mixture identified as Methyl Ester ES® available from Vaport, Inc., Portsmouth, Va. The mixture contains from about 20–25% palmitic acid ester, 25–35% oleic acid ester and 40–50% linoleic acid ester, the exact amount of each ester depending upon the type of cotton from which the seed is obtained, conditions of its growth, and other factors, and the source of the esters derived from a particular cottonseed oil. For optimum skin conditioning it is critical that the ester of the diolefinic fatty acid be present in an amount no more than 60% by weight in the vegetable oil source, and that it be essentially free of a triolefinic fatty acid ester such as linolenic acid, that is, having less than 5% by wt of linolenic acid $C_{18}H_{30}O_2$, or $CH_3[CH_2-CH=CH]_3(CH_2)_7COOH$.

Ignoring the concentration of fatty acids present in an amount less than 5% by wt, typical distributions of palmitic, oleic, linoleic and linolenic acids for commonly available vegetable oils are set forth below in Table 1.

TABLE 1

| Oil | Palmitic | Oleic | Linoleic | Linolenic |
|---|---|---|---|---|
| Arachis (peanut) | 8.5 | 51.6 | 26. | — |
| Cottonseed | 23.4 | 31.6 | 45. | — |
| Maize | 6. | 44. | 48. | — |
| Linseed | 6. | — | 74. | 17. |
| Soybean | 11. | 20. | 64. | 3. |

The proportion of higher fatty acids present in a preferred nail polish remover formulation is from 55–70% and the lower alkyl lactate is present in an amount from 30–45%. The relative amounts, in parts by weight, of higher fatty acids and ethyl lactate in three preferred formulations are set forth in Table 2 below:

TABLE 2

| Formulation # | Higher fatty acids | Ethyl lactate |
|---|---|---|
| Formulation 1 | 70 | 30 |
| Formulation 2 | 60 | 40 |
| Formulation 3 | 55 | 45 |

Though each of the formulations is effective to remove the dried nail polish in less than 1 minute, most preferred is #2 containing 60% of higher fatty acid esters derived from cottonseed oil in which about 81.6% by wt are monoolefinic and diolefinic fatty acids, and 40% ethyl lactate derived from corn oil.

The nail polish remover may be thickened by mixing with from about 5–10% by wt of a naturally occurring wax to form a gel which does not flow when coated onto a polished nail. Readily available naturally occurring waxes include candelilla wax, berry wax, beeswax, soy wax, carnauba wax, and montan wax which when dissolved in the combination of solvents allows a heavy coating of the nail polish remover to be placed on one's nails.

The nail polish remover may be colored with a color of choice, one preferably chosen from colorants and dyes approved for food, drug and cosmetic applications, exemplified by Neelicert FD&C Yellow 5, FD&C Blue #1 powder, Red 3 18% liquid solution, and the like.

The nail polish remover may be scented with a fragrance of choice, one preferably chosen from a commercially available fragrance approved for cosmetic applications, exemplified by Odor Modifier #10131.OS Apricot.

Comparison of the novel nail polish remover with a nail polish remover in which the higher fatty acid ester is methyl soyate only:

Finger nails are coated with two Revlon® nail polishes, #8053 Blackberry #14 and Super Top Speed Chrome #9448-03 Bloomchrome 007, respectively, and allowed to dry for 80 min after which each was dry to the touch. Each of the dried polishes is then removed with three different nail polish removers, namely:

(#1) a commercially available acetone-free Quick & Gentle Cutex® nail polish remover which is stated on the label to be formulated with ethyl acetate, propylene carbonate, ethyl alcohol, dimethyl glutarate, glycerin, isopropyl alcohol and fragrance as the main ingredients;

(#2) the aforementioned most favored liquid formulation #2 free of colorants, emollient, thickener or fragrance; and, (#3) a nail polish remover formulated by mixing 60 parts by wt of methyl soyate with 40 parts by wt of ethyl lactate, free of colorants, emollient, thickener or fragrance.

Each of the two nail polishes is coated on finger nails by coating the liquid with a brush, and dried six (6) times at successive intervals of 80 minutes, then removing the dried polish after each coating by swabbing the liquid, at room temperature, with a cotton towel on the coated finger nails.

Each time, the Cutex liquid (#1) begins to dissolve the dried nail polish substantially immediately and the dissolved nail polish is wiped off the finger nail after 15 sec with a cotton towel leaving a clean and dry finger nail with no visible residue. After the first application of nail polish and its subsequent removal, the finger nails look and feel normal, and the cuticle and skin surrounding the nail does not feel dry or irritated. However, after the sixth application, the finger nails look and feel dried out, and the cuticle and skin surrounding the nails feel dry and irritated.

The foregoing procedure of coating the finger nails with nail polish, drying the polish, then removing the polish, is repeated with the novel nail polish remover (#2) six times, at intervals of 80 minutes, as before. Each time the liquid (#2) fails to dissolve the dried nail polish visibly until about 5 seconds, but after an additional 5 sec, the dissolved nail polish is readily wiped off the finger nails with a cotton towel leaving clean and dry finger nails but with an unsightly, oily residue. After this procedure is repeated six times at intervals of 80 minutes, the finger nails look glossy and feel normal; moreover, the cuticle and skin surrounding the nails do not feel dry and irritated. The gloss, which does not have an oily feel, is due to a visible residue from about 2 $\mu$m to 5 $\mu$m (micrometers) thick. If the gloss is not desired, the residue may be removed by washing with a common hand soap and water.

Again, the foregoing procedure of coating the finger nails with nail polish, drying the polish, then removing the polish, is repeated with the formulated remover (#3) six times, at intervals of 80 minutes, as before. Each time the liquid (#3) fails to dissolve the dried nail polish visibly until about 5 seconds after the liquid is applied, but after an additional 10 sec, the dissolved nail polish is readily wiped off the finger nails with a cotton towel leaving dry finger nails but with an unsightly, oily residue on the surfaces. After this procedure is repeated six times at intervals of 80 minutes, the finger nails feel oily and look unsightly, moreover, the cuticle and skin surrounding the nails feel dry and irritated.

Having thus provided a general discussion, described the nail polish remover in detail and illustrated the invention with a specific illustration of the best mode of making and using it, it will be evident that the invention has provided an effective solution to an age-old problem. It is therefore to be understood that no undue restrictions are to be imposed by reason of the specific embodiments illustrated and discussed, and particularly that the invention is not restricted to a slavish adherence to the details set forth herein.

I claim:

1. A nail polish remover consisting essentially of (i) from 55% to about 70% by weight of a mixture of from about 20–25% palmitic acid ester, 25–35% oleic acid ester and 40–50% linoleic acid ester, (ii) from 30%–45% by weight of a lower ($C_{1-C5}$) alkyl lactate, and (iii) from 5 to 10% by wt of a naturally occurring wax selected from the group consisting of candelilla wax, berry wax, beeswax, soy wax, carnauba wax, and montan wax, wherein the nail polish consists essentially of a pigment and a film-forming binder selected from the group consisting of a lacquer and an enamel, each selected from the group consisting of a nitrate of cellulose and an acrylic polymer and whereby, after removal of the polish six times from finger nails, at intervals of 80 minutes, the finger nails look glossy and feel normal.

2. A nail polish remover consisting essentially of (i) a major proportion by weight ("by wt") of esters of fatty acids having from 16 to 18 carbon atoms wherein the content of linoleic acid ester in the source vegetable oil is less than 60%, (ii) a minor proportion by weight of a lower ($C_1$–$C_5$) alkyl lactate, and including from 5 to 10% by wt of a naturally occurring wax selected from the group consisting of candelilla wax, berry wax, beeswax, soy wax, carnauba wax, and montan wax, wherein the nail polish consists essentially of a pigment and a film-forming binder selected from the group consisting of a lacquer and an enamel, each selected from the group consisting of a nitrate of cellulose and an acrylic polymer and whereby, after removal of the polish six times from finger nails, at intervals of 80 minutes, the finger nails look glossy and feel normal.

3. The nail polish remover of claim 1 including from 0 to 1% by wt of a cosmetic enhancer selected from the group consisting of a color additive and a fragrance.

4. The nail polish remover of claim 1 remaining as a visible residue on a finger nail, the residue having a thickness in the range from about 2 $\mu$m to 5 $\mu$m thick.

5. The nail polish remover of claim 2 including from 0 to 1% by wt of a cosmetic enhancer selected from the group consisting of a color additive and a fragrance.

6. The nail polish remover of claim 2 remaining as a visible residue on a finger nail, the residue having a thickness in the range from about 2 $\mu$m to 5 $\mu$m thick.

7. The nail polish remover of claim 2 wherein the a major proportion by wt of the fatty acid esters have at least two double bonds, the $C_{16}$–$C_{18}$ fatty acid esters may contain contaminant higher fatty acid esters having from 12 to 14 carbon atoms and from 20–24 carbon atoms which contaminant higher fatty acid esters are together present in an amount less than 10% by wt of all the higher fatty acid esters.

* * * * *